United States Patent
Cummings et al.

(10) Patent No.: US 6,692,763 B1
(45) Date of Patent: *Feb. 17, 2004

(54) METHODS FOR TREATING POSTMENOPAUSAL WOMEN USING ULTRA-LOW DOSES OF ESTROGEN

(75) Inventors: Steven R. Cummings, Mill Valley, CA (US); Bruce Ettinger, San Francisco, CA (US); Herman Ellman, Mountain Lakes, NJ (US)

(73) Assignees: The Regents of the University of California, Oakland, CA (US); Kaiser Foundation Health Plan, Inc., Oakland, CA (US); The Permanente Medical Group, Inc., Oakland, CA (US); Berlex Laboratories, Inc., Richmond, CA (US)

(*) Notice: Subject to any disclaimer, the term of this patent is extended or adjusted under 35 U.S.C. 154(b) by 0 days.
This patent is subject to a terminal disclaimer.

(21) Appl. No.: 09/554,789

(22) PCT Filed: Nov. 21, 1998

(86) PCT No.: PCT/US98/24677
§ 371 (c)(1),
(2), (4) Date: Jul. 11, 2000

(87) PCT Pub. No.: WO99/26631
PCT Pub. Date: Jun. 3, 1999

(51) Int. Cl.[7] .......................... A61F 13/00; A61K 9/48; A61K 9/20; A61K 31/56; A61M 1/00
(52) U.S. Cl. .................. 424/449; 425/451; 425/464
(58) Field of Search .................. 424/443, 449, 424/464; 514/178

(56) References Cited

U.S. PATENT DOCUMENTS

| | | | |
|---|---|---|---|
| 3,797,494 A | 3/1974 | Zaffaroni | 424/434 |
| 4,031,894 A | 6/1977 | Urquhart et al. | 424/448 |
| 4,096,254 A * | 6/1978 | Benson et al. | |
| 4,460,372 A | 7/1984 | Campbell et al. | 424/449 |
| 4,573,996 A | 3/1986 | Kwiatek et al. | 424/434 |
| 4,624,665 A | 11/1986 | Nuwayser | 604/307 |
| 4,722,941 A | 2/1988 | Eckert et al. | 514/784 |
| 5,188,835 A * | 2/1993 | Lindskog et al. | |
| 5,223,261 A | 6/1993 | Nelson et al. | 424/443 |
| 5,460,820 A | 10/1995 | Ebert et al. | 424/449 |
| 5,891,868 A * | 4/1999 | Cummings et al. | |

FOREIGN PATENT DOCUMENTS

| | | | |
|---|---|---|---|
| EP | 0 569 338 | * | 5/1993 |
| EP | 569 338 | | 11/1993 |

OTHER PUBLICATIONS

Balfour et al., "Transdermal Estradiol . . . ," *Drugs*, 40(4):561–582 (1990).

Ettinger et al., "Long–Term Estrogen Replacement Therapy Prevents Bone Loss and Fractures," *Ann. Int. Med.*, 102:319–324 (1985).

Ettinger et al., "Prostmenopausal Bone Loss is Prevented by Treatment with Low–Dosage Estrogen with Calcium," *Ann. Int. Med.*, 106:40–45 (1987).

Ettinger et al., "Low–dosage micronized 17β–estradiol prevents bone loss in postmenopausal women," *Am. J. Obst. Gyn.*, 166(2):479–488 (1992).

(List continued on next page.)

*Primary Examiner*—Thurman K. Page
*Assistant Examiner*—Isis Ghali
(74) *Attorney, Agent, or Firm*—Townsend and Townsend and Crew LLP

(57) ABSTRACT

The present invention provides methods for treating physical conditions resulting from postmenopausel estrogen decline in a postmenopausel subject, and in particular methods for reducing the risk of osteoporotic bone fractures in a postmenopausal subject. The present invention also provides a kit for carrying out the methods of the present invention.

23 Claims, 2 Drawing Sheets

OTHER PUBLICATIONS

Evans et al., "Low and conventional dose transdermal oestradiol are equally effective at preventing bone loss in spine and femur at all postmenopausal ages," *Clin. Endo.*, 44:79–84 (1996).

Hillard et al., "Long–Term Effects of Transdermal and Oral Hormone Replacement Therapy on Postmenopausal Bone Loss," *Osteoporosis Int.*, 4:341–348 (1994).

Horsman et al., "The Effect of Estrogen Dose on Post–menopausal Bone Loss," *N. Eng. J. Med.*, 309(23):1405–1407 (1983).

Lindsay et al., "The Minimum Effective Dose of Estrogen for Prevention of Postmenopausal Bone Loss," *Obst. Gyn.*, 63(6):759–763 (1984).

Naessen et al., "Bone Loss in elderly women prevented by ultralow doses of parental 17β–estradiol," *Am. J. Obst. Gyn.*, 177(1):115–119 (1997).

Stevenson et al., "Effects of transdermal versus oral hormone replacement therapy on bone density in spine and proximal femur in postmenopausal women," *The Lancet*, 336:265–269 (1990).

Tepper et al., "Estrogen Replacement in Postmenopausal Women: Are We Currently Overdosing Our Patients," *Gyn. Obst. Invest.*, 38:113–116 (1994).

* cited by examiner

METHODS FOR TREATING POSTMENOPAUSAL WOMEN USING ULTRA-LOW DOSES OF ESTROGEN

BACKGROUND OF THE INVENTION

Endogenous estrogens fall dramatically after natural or surgical menopause, and this decline results in a marked increase in bone loss and subsequent fractures. Endogenous estrogens are clearly important for the maintenance of skeletal health in younger women. However, the importance of endogenous estrogens in older women is less certain.

It has been previously shown that endogenous estrone levels in women over age 65 were not associated with subsequent hip or vertebral fractures. S. R. Cummings, et al., *J. Bone Min. Res.* 10 (Suppl I):S174 (1995). However, estradiol is a more potent estrogen that estrone, and studies of its relationship to fractures have been inconclusive. Serum estradiol levels in premenopausal women average over 100 pg/ml. Serum estradiol levels in postmenopausal women not being treated with hormone replacement therapy fall below 20 pg/ml and as many as 30–50 percent of postmenopausal women have serum estradiol levels which are undetectable by conventional, sensitive assay methods (i.e., less than 5 pg/ml). Conventional treatment for postmenopausal women includes estrogen replacement therapy in doses sufficient to maintain serum estradiol levels above 40–60 pg/ml.

Conventional hormone replacement therapy has proven useful for treating physical conditions resulting from postmenopausal estrogen decline, including reducing the loss of, or even increasing bone density; and decreasing the risk of bone fracture. However, studies have indicated that hormone replacement therapy may be linked to increased risk of breast and endometrial cancers, as well as blood clotting and bleeding from the uterus. Accordingly, there remains a need in the art for methods of treating the physical conditions which result from postmenopausal estrogen decline or deficiency. There also remains a need in the art for treating such physical conditions while reducing the side effects of hormone replacement therapy.

SUMMARY OF THE INVENTION

As a first aspect, the present invention provides a method for treating physical conditions resulting from estrogen decline in a postmenopausal subject. The method comprises administering to the subject, an amount of estrogen which is effective to produce a serum estradiol level of between about 5 pg/ml and about 15 pg/ml.

As a second aspect, the present invention provides a method for reducing the risk of osteoporotic bone fractures in a subject afflicted with or susceptible to postmenopausal osteoporosis. The method comprises administering to the subject, an amount of estrogen which is effective to produce a serum estradiol level of between about 5 pg/ml and about 15 pg/ml.

As a third aspect, the present invention provides a kit for use by a consumer afflicted with or susceptible to physical conditions resulting from postmenopausal estrogen decline. The kit comprises a) a transdermal patch capable of transdermally administering less than about 20 µg of estrogen per day; and b) instructions describing a method of using the transdermal patch to reduce the risk of bone fracture in the consumer.

As a fourth aspect, the present invention provides another method for treating physical conditions resulting from postmenopausal estrogen decline in a postmenopausal subject. The method includes administering less than about 20 µg of estrogen per day in the absence of exogenous progestin.

As a fifth aspect, the present invention provides another method for reducing the risk of osteoporotic bone fractures in a subject afflicted with or susceptible to osteoporosis. The method includes administering less than about 20 µg of estrogen per day in the absence of exogenous progestin.

These and other aspects of the present invention are described further in the drawings, description of the preferred embodiment and examples of the invention which follow.

DESCRIPTION OF THE PREFERRED EMBODIMENT

Figure 1:
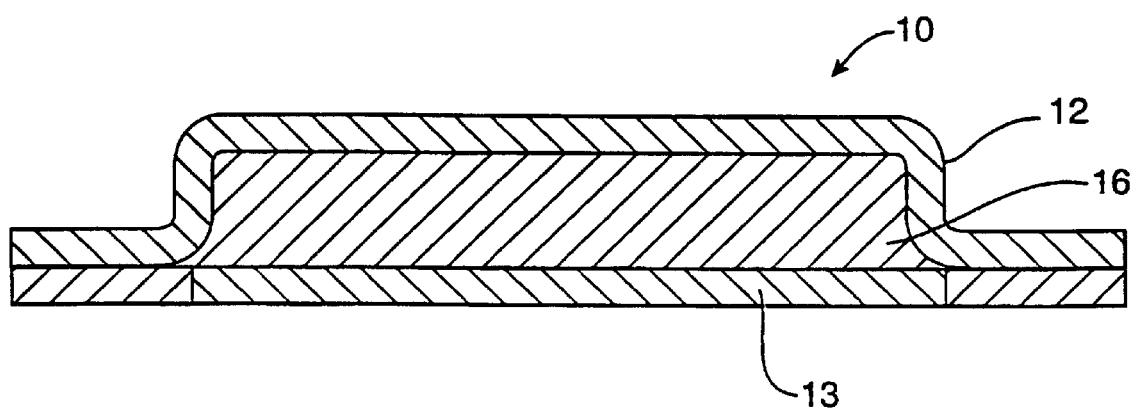
FIG. 1 is a cross-sectional view of one type of transdermal patch which may be employed in the methods of the present invention.

Unless otherwise defined, all technical and scientific terms employed herein have their conventional meaning in the art. As used herein, the following terms have the means ascribed to them.

"Physical conditions resulting from postmenopausal estrogen decline" refers to physical conditions which are common among postmenopausal women and which are caused, at least in part, by a decline in estrogen in the body. These conditions include but are not limited to osteoporosis, headaches, nausea, depression, hot flashes, decrease in bone mineral density, and increased risk or incidence of bone fracture, including vertebral and/or hip fracture.

"Postmenopausal subject" refers to women in the period of life after menopause. Subjects afflicted with postmenopausal symptoms include women after menopause who exhibit any of the foregoing physical conditions after menopause, and particularly women after menopause who exhibit decreased bone mineral density, in the vertebrae, hip or other site, or who have experienced either vertebral or hip fracture. Subjects susceptible to physical conditions resulting from postmenopausal estrogen decline include women approaching the onset of menopause who are exhibiting a decrease in serum estradiol levels as compared to premenopausal women, and women after menopause who are exhibiting a decrease in serum estradiol levels but who have not yet exhibited physical conditions caused by postmenopausal estrogen decline. Subjects exhibiting decreased serum estradiol levels include subjects exhibiting a serum estradiol level at or below 20 pg/ml, including subjects exhibiting undetectable levels of serum estradiol. For purposes of this invention, sex hormone levels, including serum estradiol levels were measured using by radioimmunoassay after extraction and column separation. The lower limit of detectability is 5 pg/ml of estradiol.

"Osteoporotic bone fractures" refers to bone fractures, typically in the vertebrae or hip for which osteoporosis is a contributing factor.

The methods of the present invention are useful for the treatment of postmenopausal subjects, particularly subjects afflicted with or susceptible to postmenopausal physical conditions of the type discussed hereinabove. The methods of the present invention involve the administration of estrogen in an amount effective to produce the desired serum estradiol level in the subject. As used herein, the phrase "treating physical conditions" contemplates eliminating or reducing the severity or incidence of such physical conditions in the subject afflicted with such conditions, and also preventing the occurrence of postmenopausal physical conditions in a subject susceptible to such conditions as a result of postmenopausal estrogen decline. Although treatment of these postmenopausal physical conditions may include the complete elimination of such conditions in a subject afflicted therewith, complete elimination of the condition is not required to meet the definition of the term which is contemplated by the instant invention. Thus, the present invention involves the use of ultra-low doses of estrogen for the treatment of physical conditions resulting from estrogen decline and for reducing the risk of osteoporotic bone fractures in a subject afflicted with or susceptible to postmenopausal osteoporosis.

The methods of the present invention may also include the additional step of testing the serum estradiol level of the postmenopausal subject to be treated and determining that the serum estradiol level of the subject to be treated is normal for postmenopausal women in the same age group as the subject. In other words, the methods of the present invention are not reserved for treatment of women having lower than normal serum estradiol levels than the average of postmenopausal women in the same age group. The methods of the present invention may be used to treat postmenopausal subjects whose serum estradiol is normal for postmenopausal women of the same age group. As used herein, a "normal" serum estradiol level is a serum estradiol level which is relatively close to the average serum estradiol level for women of the same age group.

The present inventors have unexpectedly discovered that loss of bone mineral density is not the only contributing factor leading to an increased risk of osteoporotic bone fractures in subjects afflicted with postmenopausal osteoporosis. Low levels of serum estradiol, i.e., below 5 pg/ml, especially when accompanied by sex hormone binding globulin (SHBG) levels of 1 $\mu$g/dl or more substantially increase the risk of hip and vertebral fractures. In addition, low serum levels of $1,25(OH)_2$ Vitamin D also leads to increased risk of hip fractures. The method of assessing the risk of osteoporotic bone fractures involves the use of logistic models developed by SAS Institute, Cary, N.C., to analyze the relationship between predictors and vertebral fractures, and proportional hazards models that take into account the case-cohort sampling design to analyze the relationship between predictors and hip fractures. The analyses are adjusted for baseline age and weight, and reported as relative risks with 95% confidence intervals. The proportion of fractures attributed to various hormone levels are estimated using the technique described in W. S. Browner, *American Journal of Epidemiology* 123:143 (1986), the disclosure of which is incorporated herein by reference in its entirety. By "reducing the risk of osteoporotic bone fracture" is meant that the risk, as measured using the foregoing techniques, is lower for a given subject who is treated with the methods of the present invention, as compared to the risk for the same subject prior to treatment using the methods of the present invention. Thus, the risk of osteoporotic bone fractures is reduced for a subject treated with the methods of the present invention as compared to an untreated postmenopausal subject afflicted with or susceptible to osteoporotic bone fractures.

The present inventors have also unexpectedly discovered that the treatment of physical conditions resulting from estrogen decline can be affected by ultra low doses of estrogen without the need for administration of progestin. The administration of estrogen, excluding the administration of progestin has now been found by the present inventors to be effective for treatment of postmenopausal women who have a uterus and ovaries. Previous hormone replacement therapies have relied upon the co-administration of progestin for effective treatment, particularly of women who have not undergone hysterectomy or ovariectomy.

The source of exogenous estrogen for use in the methods of the present invention may include any suitable form of estrogen for administration to a subject. Suitable forms of exogenous estrogen include both natural and synthetic compounds exhibiting estrogenic activity. Several forms of exogenous estrogen are commercially available. For example, suitable forms of exogenous estrogen include but are not limited to estradiols, including $\alpha$-estradiol, $17\beta$-estradiol, ethinyl estradiol, estradiol benzoate, and estradiol $17\beta$-cypionate; estrone; estriol; conjugated equine estrogens; and salts of the forgoing. The foregoing are all examples of steroids which exhibit estrogenic activity. Examples of nonsteroidal compounds exhibiting estrogenic activity include but are not limited to diethylstilbestrol diphosphate, diethylstilbestrol dipropionate, and hexestrol. Currently, the preferred form of exogenous estrogen for use in the methods of the present invention is estradiol.

The amount of exogenous estrogen to be administered to the subject is sufficient to achieve a serum estradiol level of at least about 5 pg/ml but not more than about 20 pg/ml and preferably not more than 15 pg/ml. In other words, according to the methods of the present invention, sufficient exogenous estrogen is administered to achieve a total serum estradiol level of at least about 5 pg/ml/ml and about 20 pg/ml. Since the serum estradiol level of an untreated subject will differ for each individual, different individuals may require administration of different doses of estrogen to achieve the required serum estradiol level. It is not required that the serum estradiol level of each subject being treated be increased by between about 5 and about 20 pg/ml; rather the total serum estradiol level of each treated subject must be at least about 5 and not more than about 20 pg/ml. Often, the amount of exogenous estrogen to be administered is sufficient to achieve a serum estradiol level of between about 5 pg/ml and about 10 pg/ml. Contrary to previous understanding, the present inventor(s) have now discovered that serum estradiol levels of between 5 pg/ml and 15 pg/ml advantageously produce a decrease in the risk of vertebral and hip fracture. The administration of this lower than conventional amount of exogenous estrogen has the further advantage of decreasing the risk of undesirable side effects associated with hormone replacement therapy.

The administration of exogenous estrogen can be accomplished by any suitable route. For example, formulations for oral and parenteral administration of exogenous estrogen are known in the art, and may be employed in the methods of the present invention. Formulations suitable for oral administration may be presented in discrete units, such as capsules, cachets, lozenges, or tablets, each containing a predetermined amount of the active compound; as a powder, or granules; or as a solution, dispersion, or suspension in an aqueous or non-aqueous liquid. Such formulations may be prepared by any suitable method of pharmacy which includes the step of bringing into association the active compound and a suitable carrier (which may contain one or more accessory ingredients). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding in a suitable tableting machine, the powdered compound moistened with an inert liquid binder.

The amount of exogenous estrogen in the oral formulation is an ultra-low dose of estrogen which will depend upon the precise form of estrogen to be administered, but is typically less than 0.5 mg per day. Preferably, the amount of estrogen administered orally is between about 0.1 mg and about 0.25 mg of estrogen per day. For example, the amount of estradiol administered orally is from about 0.1 mg to about 0.25 mg per day. It is well within the skill of those in the art to determine equivalent dosages of other forms of estrogen as well.

In the preferred embodiments of the present invention, estrogen is administered parenterally or transdermally rather than orally. The former routes of administration are preferred over oral administration because oral administration of estrogen may lead to increased levels of sex hormone binding globulin. Sex hormone binding globulin may diminish the beneficial effects of administering estrogen to postmenopausal subjects, particularly subjects exhibiting signs of osteoporosis or loss of bone mineral density. Although oral administration is not the preferred route, the methods of the present invention may be carried out using oral formulations.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, intradermal injection, or vaginal ring. Such preparations may conveniently be prepared by admixing the active ingredient, an estrogen, with water or a glycine buffer and rendering the resulting solution sterile and isotonic with the blood.

The amount of exogenous estrogen in the parenteral formulation is an ultra-low dose of estrogen which will depend upon the precise form of estrogen to be administered, but is typically not more than 20 $\mu$g per day. Preferably, the amount of estrogen administered parenterally is between about 5 $\mu$g and about 15 $\mu$g of estrogen per day, and more preferably about 10 $\mu$g of estrogen per day. For example, the amount of estradiol administered parenterally is from about 5 $\mu$g to about 15 $\mu$g per day. It is well within the skill of those in the art to determine equivalent dosages of other forms of estrogen as well.

More preferably, the methods of the present invention include the transdermal administration of exogenous estrogen. Suitable formulations for the transdermal administration of estrogen are known in the art, and may be employed in the methods of the present invention. For example, suitable transdermal patch formulations for the administration of exogenous estrogen is described in U.S. Pat. No. 4,460,372 to Campbell et al., U.S. Pat. No. 4,573,996 to Kwiatek et al., U.S. Pat. No. 4,624,665 to Nuwayser, U.S. Pat. No. 4,722,941 to Eckert et al., and U.S. Pat. No. 5,223,261 to Nelson et al., the disclosures of which are hereby incorporated by reference for their discussion of transdermal patch technology.

One suitable type of transdermal patch for use in the methods of the present invention is shown in FIG. 1. In general, a suitable transdermal patch 10 includes a backing layer 12 which is non-permeable, a permeable surface layer 13, an adhesive layer (not shown) substantially continuously coating the permeable surface layer 13, and a reservoir 16 located or sandwiched between the backing layer 12 and the permeable surface layer 13 such that the backing layer 12 extends around the sides of the reservoir 16 and is joined to the permeable surface layer 13 at the edges of the permeable surface layer 13. The reservoir 16 contains estrogen and is in fluid contact with the permeable surface layer 13. The transdermal patch 10 is adhered to the skin by the adhesive layer on the permeable surface layer 13, such that the permeable surface layer 13 is in substantially continuous contact with the skin when the transdermal patch 10 is adhered to the skin. While the transdermal patch 10 is adhered to the skin of the subject, the estrogen contained in the reservoir 16 of the transdermal patch 10 is transferred via the permeable surface layer 13, from the reservoir 16, through the adhesive layer, and to and through the skin of the subject. The transdermal patch 10 may optionally also include one or more penetration-enhancing agents in the reservoir 16 that enhance the penetration of the estrogen through the skin.

Examples of suitable materials which may comprise the backing layer are well known in the art of transdermal patch delivery, and any conventional backing layer material may be employed in the transdermal patch of the instant invention. Specific examples of suitable backing layer materials include but are not limited to polyester film, such as high density polyethylene, low density polyethylene or composites of polyethylene; polypropylene; polyvinyl chloride, polyvinylidene chloride; ethylene-vinyl acetate copolymers; and the like.

Examples of suitable permeable surface layer materials are also well known in the art of transdermal patch delivery, and any conventional material which is permeable to the active ingredient to be administered, i.e., estrogen, may be employed in the transdermal patch of the instant invention. Specific examples of suitable materials for the permeable surface layer include but are not limited to dense or microporous polymer films such as those comprised of polycarbonates, polyvinyl chlorides, polyamides, modacrylic copolymers, polysulfones, halogenated polymers, polychloroethers, acetal polymers, acrylic resins, and the like. Specific examples of these types of conventional permeable membrane materials are described in U.S. Pat. No. 3,797,494 to Zaffaroni.

Examples of suitable adhesives which may be coated on the backing layer to provide the adhesive layer are also well known in the art and include, for example pressure sensitive adhesives such as those comprising acrylic and/or methacrylic polymers. Specific examples of suitable adhesives include polymers of esters of acrylic or methacrylic acid (e.g., n-butanol, n-pentanol, isopentanol, 2-methyl butanol, 1-methyl butanol, 1-methyl pentanol, 3-methyl pentanol, 3-methyl pentanol, 3-ethyl butanol, isooctanol, n-decanol, or n-dodecanol esters thereof) alone or copolymerized with ethylenically unsaturated monomers such as acrylic acid, methacrylic acid, acrylamide, methacrylamide, N-alkoxymethyl acrylamides, N-alkoxymethyl methacrylamides, N-t-butylacrylamide, itaconic acid, vinyl acetate, N-branched $C_{10-24}$ alkyl maleamic acids, glycol diacrylate, or mixtures of the foregoing; natural or synthetic rubbers such as silicon rubber, styrene-butadiene rubber, butyl-ether rubber, neoprene rubber, nitrile rubber, polyisobutylene, polybutadiene, and polyisoprene; polyurethane elastomers; vinyl polymers such as polyvinyl alcohol, polyvinyl ethers, polyvinyl pyrrolidone, and polyvinyl acetate; ureaformaldehyde resins; phenol formaldehyde resins; resorcinol formaldehyde resins; cellulose derivatives such as ethyl cellulose, methyl cellulose, nitrocellulose, cellulose acetatebutyrate, and carboxymethyl cellulose, and natural gums such as guar, acacia, pectin, starch, destria, gelatin, casein, etc. As will be apparent to those skilled in the art, the adhesive layer should be inert to the active ingredient, estrogen, and should not interfere with the transdermal delivery of the estrogen through the permeable surface layer. Pressure sensitive adhesives are preferred for the adhesive layer of the transdermal patch to facilitate the application of the patch to the skin of the subject.

Suitable penetration-enhancing agents are well known in the art as well. Examples of conventional penetration-enhancing agents include alkanols such as ethanol, hexanol, cyclohexanol, and the like; hydrocarbons such as hexane, cyclohexane, isopropylbenzene; aldehydes and ketones such as cyclohexanone, acetamide; N,N-di(lower alkyl) acetamides such as N,N-diethylacetamide, N,N-dimethyl acetamide,; N-(2-hydroxyethyl) acetamide; esters such as N,N-di-lower alkyl sulfoxides; essential oils such as propylene glycol, glycerine, glycerol monolaurate, isopropyl myristate, and ethyl oleate; salicylates; and mixtures of any of the above.

Figure 2:
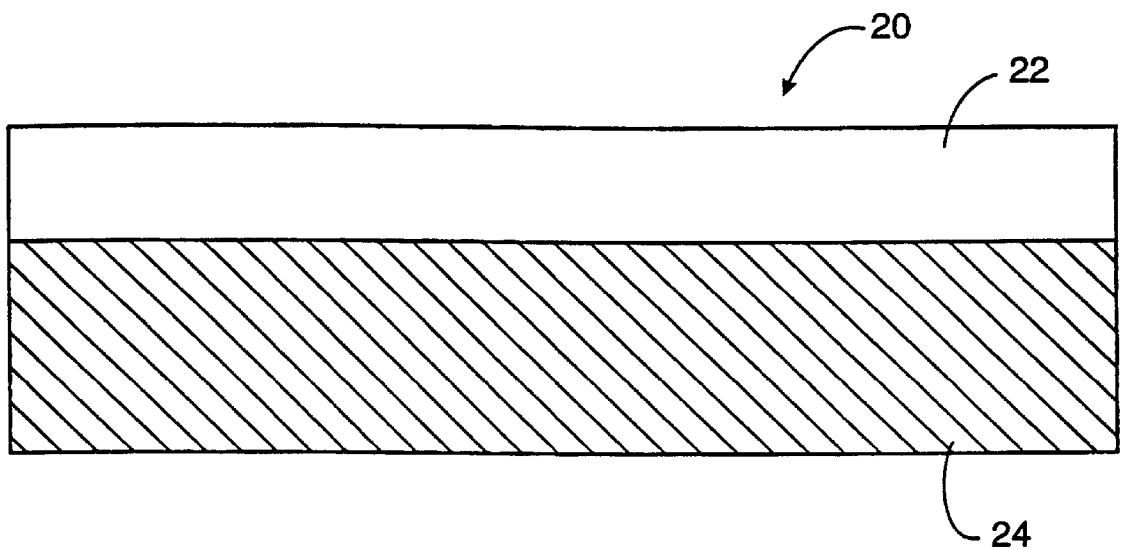
FIG. 2 is a cross-sectional view of a second type of transdermal patch which may be employed in methods of the present invention.

FIG. 2 is an example of second type of transdermal patch which is suitable for the transdermal delivery of estrogen according to the present invention. In this example, the active ingredient is incorporated in to the adhesive layer rather than being contained in a reservoir. Examples of these types of patches are conventionally known and include, for example, the CLIMERA® patch available from Berlex. The transdermal patch 20 comprises a backing layer 22 and an adhesive/drug layer 24. The adhesive/drug layer 24 has the combined function of adhering the patch 20 to the skin of the subject and containing the active ingredient, estrogen, which is to be administered. The active ingredient is leached from the adhesive/drug layer 24 to and through the skin of the subject when the patch is adhered to the skin.

Any of the backing layers described herein above may be employed in this embodiment as well. In addition, any of the suitable adhesives described above may be employed. The adhesive/drug layer comprises a relatively homogeneous mixture of the selected adhesive and the active ingredient. Typically, the adhesive/drug layer comprises a coating substantially covering one surface of the backing layer. The adhesive/drug layer may also include a penetration enhancing agent such as those described above by incorporating the penetration enhancing agent into the substantially homogeneous mixture of the adhesive and the active ingredient.

As will be readily apparent to those skilled in the art, the transdermal patches according to the present invention may include a variety of additional excipients which are conventionally employed to facilitate the transdermal administration of an active agent, particularly a steroidal active agent. Examples of such excipients include but are not limited to carriers, gelling agents, suspending agents, dispersing agents, preservatives, stabilizers, wetting agents, emulsifying agents, and the like. Specific examples of each of these types of excipients are well known in the art and any conventional excipients may be employed in the transdermal patches of the instant invention. It is important to note, however, that the transdermal patches of the present invention exclude progestins. Accordingly, progestin is not a suitable excipient for use in the transdermal patch formulations of the present invention.

The amount of exogenous estrogen in the transdermal patch formulations is an ultra-low dose of estrogen which will depend upon the precise form of estrogen to be administered, but is sufficient to deliver less than 20 $\mu$g, and typically not more than 15 $\mu$g per day. Preferably, the amount of estrogen administered via the transdermal patch is between about 5 $\mu$g and about 15 $\mu$g of estrogen per day. More preferably, the amount of estrogen administered is about 10 $\mu$g per day. Although the typical dose of estrogen according to the method of the present invention is less than 20 $\mu$g, doses as high as 25 $\mu$g may be employed. For example, the amount of estradiol administered parenterally is from about 5 $\mu$g to about 15 $\mu$g per day. It is well within the skill of those in the art to determine equivalent dosages of other forms of estrogen as well. The ultra-low level of estrogen employed in the methods of the present invention has unexpectedly been found to substantially reduce the risk of osteoporotic bone fractures in postmenopausal women.

Typically, the transdermal patches are designed to be worn for several days before replacement is required. Thus the amount of estrogen in the reservoir must be sufficient to permit the administration of less than 20 $\mu$g per day for a period of several days. As an example, a transdermal patch according to the present invention which is designed to administer 10 $\mu$g of estrogen per day for seven (7) days would contain approximately 1 mg of estrogen. A patch suitable for the administration of 15 $\mu$g per day for seven (7) days would contain approximately 1.4 mg of estrogen. Based upon these specific examples, one skilled in the art would be able to discern the necessary amount of estrogen to be included in the transdermnal patch to achieve the delivery of the correct daily dose of estrogen.

Advantageously, the present invention also provides a kit for use by a consumer afflicted with or susceptible to postmenopausal symptoms which includes the transdermal patch and instructions describing the method of using the transdermal patch to treat postmenopausal symptoms and/or reduce the risk of osteoporotic bone fracture in the consumer. The instructions would direct the consumer to adhere the transdermal patch, using the adhesive thereon, directly to the skin surface, for example at the upper arm, to achieve the transdermal administration of the ultra-low dose of estrogen from the patch and thereby increase the serum estradiol level in the consumer to between about 5 pg/ml and about 20 pg/ml. The instructions would also direct the consumer to replace the patch as required to continue the administration of estrogen as necessary to maintain this serum estradiol level by using the transdermal patch. In particular, the instructions might direct the consumer to replace the transdermal patch every seven (7) day to ensure the administration of less than 20 $\mu$g, and preferably 10 $\mu$g of estrogen per day when a seven-day patch is utilized in the kit. Such kits could advantageously be packaged and sold in single or multiple patch units.

The following example is provided to illustrate the present invention, and should not be construed as limiting thereof.

EXAMPLE 1

The following example and data demonstrate the correlation between serum estradiol level and risk of osteoporotic bone fracture and also demonstrate the efficacy of using an ultra-low dose of exogenous estrogen to reduce the risk of osteoporotic bone fracture and for the treatment of postmenopausal symptoms.

1. Experimental Population

The Study of Osteoporotic Fractures is a prospective study of a cohort of 9,704 women who were recruited from population-based listings in four communities in the United States: Baltimore, Minneapolis, Pittsburgh and Portland. See, Cummings et al., *N. Engl. J. Med.* 332:767–773 (1995). Women age 65 or older were invited by mail to participate in the study. The experimental population excluded black women, because of their low risk of hip fractures, and women who had bilateral hip replacements or who needed the help of another person to walk. Participants were asked about current or recent use of estrogen, calcium supplements and multivitamins containing vitamin D.

2. Clinical Measurements

Bone mineral density (i.e., bone mass of the calcaneus) was measured using single photon absorptiometry obtained from OsteoAnalyzer, Siemens-Osteon, Wahiawa, Hi. The mean coefficient of variation for this measurement between clinical centers was 1.2%. See, Steiger, et al., *J. Bone Miner. Res.* 7:625 (1992).

3. Serum Samples

All participants were instructed to adhere to a fat free diet overnight and the morning before the examination to minimize lipemia that might interfere with assays. Blood was drawn between 8:00 AM and 2:00 PM and serum was immediately frozen to −20° C. All samples were shipped within two weeks to the Biomedical Research Institute at Rockville, Md. where they were stored in liquid nitrogen at −190° C.

4. Ascertainment of Fractures

Women were contacted every 4 months by postcard or at periodic clinic visits: follow-up for vital status and occurrence of hip fractures was more than 99.7% complete. Hip fractures were confirmed by a review of preoperative radiographs. An average of 3.3 years after the baseline radiographs were taken, 7299 women (79% of survivors) returned for repeat lateral spine films; 7238 pairs of radiographs were judged to be adequate for assessment of incident vertebral fractures. We assessed radiographs for fractures using quantitative morphometry as described in Black et al., *J. Bone Miner. Res.* 10:890 (1995). A woman was classified as having an incident vertebral fracture if any vertebral height decreased by $\geq 20\%$ and $\geq 24$ mm between baseline and follow-up radiograph. See, National Osteoporosis Foundation Working Group on Vertebral Fractures, *J. Bone Miner. Res.* 10:518 (1995). Those who assessed the radiographs had no knowledge of results of participants' serum assays.

5. Selection of Case and Cohort Samples

Using the case-cohort approach described in Prentice, R. L., *Biometrika* 73:1 (1986), and excluding women who used hormone replacement therapy at baseline, we randomly selected serum samples from 133 participants who subsequently suffered a first hip fracture and 138 from participants who had incident vertebral fractures. We also selected a random sample of 359 women from the cohort, including 12 women who had subsequent hip fracture and 14 who had subsequent vertebral fractures. For hip fracture analyses, we excluded controls (n=4) who had suffered hip fractures before the baseline visit; for vertebral fracture analyses, we excluded controls (n=8) who did not have a follow-up radiograph or whose baseline or follow-up radiograph was technically inadequate for morphometry.

6. Biochemical Analyses

We determined the stability of selected types of hormone measurements in 51 postmenopausal women by assaying levels at baseline and again after 3.5 years of storage at −190° C. Correlations (all significant at P<0.001) between the two measurements were as follows: mid-region parathyroid hormone (r=0.99), 25(OH)vitamin D (r=0.88), testosterone (r=0.99), and estrone (r=0.98). There were little, if any, declines in the mean values for these substances. An immunoradiometric assay (IRMA) for parathyroid hormone was not available when the baseline measurements were made; the correlation between levels measured by IRMA and by the mid-region technique was 0.78.

All assays were performed in mixed batches of cases and controls, blinded to a participant's history of fracture. Samples were sent directly from storage to the analytical laboratory without thawing. Initial plans called for analysis of estrone, but not estradiol, levels. After completing the first batch of assays, we added estradiol to the panel of measurements and made these measurements in 89 hip fracture cases, 96 vertebral fracture cases and 204 women who had neither type of fracture.

Sex hormones and sex hormone binding globulin (SHBG) were assayed by Endocrine Sciences of Calabasas Hills, Calif. Estradiol and estrone were measured by radioimmunoassay after extraction and 1 $H_2O$ column separation. The inter-assay variability for estradiol ranged from 8% to 12.5% and from 6.2% to 7.0% for estrone. The lower limit of detectability was 5 pg/ml for estradiol. Total testosterone was measured by radioimmunoassay after extraction and $Al_2O_3$ column chromatography with an inter-assay variability from 6.1% to 13.4%. The binding capacity of SHBG was directly measured in serum using a displacement technique with an inter-assay variability of 4.1% to 14.4%. Free testosterone concentration is determined from an ammonium sulfate precipitation procedure as described in Furuyama et al., *Steroids* 16:415 (1970); and Mayes, *J. Clin. Endocrinol. Metab.* 28:1169 (1968). The interassay variability ranged from 10.7% to 15.5%.

Calciotropic hormones were assayed by the UCSF Calciotropic Hormone Reference Laboratory of San Francisco, Calif. Intact parathyroid hormone was measured by radioimmunoassay with an intra-assay variability of 5.2% and an interassay variation of 8.5%. We measured 25(OH)vitamin D and 1,25(OH)$_2$vitamin D using radioimmunoassay techniques, with an intra-assay variability of 6.6% for both and inter-assay variabilities of 15% and 24.4% respectively. Creatinine levels were measured using an automated chemistry analyzer.

7. Data Analysis

We analyzed hormone and vitamin levels as continuous variables, by approximate quintiles, and, when relevant, as dichotomous variables (above or below the detection threshold). We used logistic models developed by SAS Institute of Cary, N.C., to analyze the relationship between predictors and vertebral fractures, and proportional hazards models that take account of the case-cohort sampling design (Epicure, Hirosoft International, Seattle, Wash.) to analyze the relationship between predictors and hip fracture. All analyses were adjusted for baseline age and weight, and are reported as relative risks (approximated as odds ratios or hazard ratios) with 95% confidence intervals. We estimated the proportion of fractures attributed to various hormone levels with standard techniques described by Browner, *Am. J. Epidemiol.* 123:143 (1986). We compared age-adjusted bone mass in different groups using general linear models.

8. Results

Table 1 sets forth the data collected regarding the characteristics of participants who suffered incident hip or vertebral fractures.

TABLE 1

Characteristics of participants with incident hip fractures, incident vertebral fractures, and controls with neither outcome.

| | Vertebral fracture | | Hip fracture | |
|---|---|---|---|---|
| Characteristic | Fracture cases (n = 138) | Cohort* sample (n = 264) | Fracture cases (n = 133) | Cohort sample (n = 343) |
| Mean age (years) | 73.2† | 71.6 | 75.3† | 72.1 |
| Mean weight (kg) | 63.5† | 68.6 | 61.9† | 68.2 |
| Current cigarette smoking | 12% | 8.8% | 17%‡ | 9.1% |
| Current calcium supplement use | 53%‡ | 42% | 51% | 42% |
| Current vitamin D supplement use | 43% | 42% | 43% | 48% |
| Mean dietary calcium intake (mg/day) | 695 | 693 | 659 | 689 |
| Mean calcaneal bone mass (g/cm$^2$) | 0.35† | 0.41 | 0.34† | 0.41 |

*Number of controls for hip fracture analysis varies from 240 to 343 because of missing data from assays for estradiol. The number of controls for vertebral fracture varies from 193 to 264; it is smaller because of exclusion of those without technically adequate pairs of baseline and follow-up vertebral x-rays. Cases of incident fracture drawn with the cohort sample are included with cases.
†P < .01 compared with controls
‡P < .05 compared with controls The data show that participants who suffered incident hip or vertebral fractures were older, weighed less, were more likely to be smokers, and had lower bone mass than controls.

About one in three (81 or 247) women in the random sample of the cohort had undetectable estradiol levels (<5 pg/ml). The data regarding relative risk, adjusted for weight and age, is set forth in Table 2 below.

TABLE 2

Age and weight-adjusted associations between hormone and vitamin levels and risk of hip fracture and vertebral fracture

| Variable | Prevalence (%)† | Relative risk (95% C.I.)* Hip fracture | Vertebral fracture |
|---|---|---|---|
| Total estradiol <5 pg/ml | 32.8 | 2.48(1.35–4.55) | 2.46(1.43–4.22) |
| Sex hormone binding globulin > 0.9 μg/dl | 76.4 | 2.04(1.06–3.85) | 2.27(1.19–4.35) |
| Sex hormone binding globulin (per 1.0 μg/dl) | | 1.25(0.97–1.60) | 1.49(1.15–1.95) |
| Estrone ≧ 1.5 ng/dl | 77.4 | 1.30(0.76–2.17) | 1.72(1.01–2.94) |
| Free testosterone ≦ 0.7 pg/ml | 19.4 | 1.63(1.00–2.66) | 1.40(0.83–2.35) |
| 25(OH)vitaminD ≦ 19 ng/ml‡ | 21.5 | 1.16(0.70–1.92) | 1.08(0.64–1.80) |
| 1,25(OH)$_2$vitamin D ≦ 23 pg/ml§ | 15.4 | 2.05(1.21–3.46) | 1.60(0.92–2.79) |
| Intact PTH > 50 pg/ml | 11.2 | 1.05(0.52–2.12) | 0.49(0.20–1.17) |

*Relative risks estimated as odds ratios for vertebral fractures and hazard ratios for hip fractures. C.I. = confidence interval.
†Prevalence in the random sample of the cohort.
‡To convert values for 25-hydroxyvitamin D top nanomoles per liter, multiply by 2.496.
§To convert values for 1.25-dihydroxyvitamin D to picomoles per liter, multiply by 2.4.

The data demonstrate that women with undetectable estradiol levels had a 2.5-fold greater risk of hip fracture and of vertebral fracture than women who had measurable levels of this hormone. We estimate that 33% of hip fractures and 32% of vertebral fractures in this cohort were associated with undetectable estradiol levels. The data appear to reflect a threshold decrease in risk associated with estradiol concentrations≧5 pg/ml. Women with total estradiol levels from 5 to 10 pg/ml had a 62% lower risk of hip fractures (hazard ratio=0.38; 0.20 to 0.72) and a 57% lower risk of vertebral fractures (odds ratio=0.43; 95% confidence interval 0.25 to 0.76) than women with levels below 5 pg/ml.

Higher levels of SHBG were associated with increasing risk of hip and vertebral fractures. After adjusting for age, each 1.0 μg/dl increase in SHBG was associated with a 1.44-fold (1.16 to 1.80) increase in the risk of hip fracture and a 1.65-fold (1.30 to 2.10) increase in the risk of vertebral fracture. For hip fracture, this effect appeared to be partly mediated by weight.

In a random sample of the cohort, 26% (63 of 244) had both an undetectable estradiol level and an SHBG level≧1 μg/dl; these women had a 14-fold greater risk of hip fracture (95% confidence interval; 3.0 to 62) and 12-fold (3.3 to 41) greater risk of vertebral fracture than other women. Adjustment for weight blunted these associations somewhat for both hip fracture (hazard ratio=6.9; 1.5 to 32) and vertebral fracture (odds ratio=7.9; 2.2 to 28). Associations between estradiol, SHBG and incident vertebral fractures were similar in the subgroups of women who had a vertebral fracture at baseline and those who did not. Attributable risk for the 26% of women with this combination was 60% for hip fractures and 64% for vertebral fractures.

The data of Table 2 regarding vertebral fractures in expanded by the data set forth in Table 3 below.

TABLE 3

Predictors of vertebral fracture: multivariable models*

| | Odds ratio (95% confidence interval) | |
|---|---|---|
| Variable (unit) | Multivariable adjusted | Also adjusted for bone mass |
| Estradiol < 5 pg/ml | 2.65 (1.50–4.68) | 2.34 (1.30–4.22) |
| SHBG (per 1 μg/dl increase) | 1.62 (1.16–2.26) | 1.51 (1.07–2.12) |
| Estrone ≧ 1.5 ng/dl | 2.04 (1.03–4.17) | 2.33 (1.12–4.76) |
| Age (per 5 year increase) | 1.17 (0.89–1.54) | 1.09 (0.82–1.44) |
| Weight (per 10 kg increase) | 0.71 (0.53–0.94) | 0.86 (0.64–1.16) |
| Calcaneal bone mass (per SD decrease)† | | 2.27 (1.52–3.33) |

*All results are adjusted for other variables in table. SD (standard deviation) of calcaneal bone is 0.098 g/cm$^2$.
†Calcaneal bone mass measured at baseline.

The data of Table 2 show that women with estrone values in the lowest quintile (≦1.4 ng/dl) had a lower risk of vertebral fracture than women with higher levels. Although women with lower estrone tended to have lower estradiol levels, the correlation between levels of estrone and estradiol was modest (r=0.57) and low levels of estrone remained associated with a decreased risk of vertebral fracture after adjustment for estradiol levels, as shown in Table 3.

Women whose 1,25(OH)$_2$vitamin D level was in the lowest quintile (≦23 pg/ml [≦55.2 pm/L]) had a significantly increased risk of hip fracture (hazard ratio 2.1; 1.2 to 3.5), as shown in Table 4 below.

TABLE 4

Predictors of hip fracture: multivariable models*

| | Hazard ratio (95% confidence interval) | |
|---|---|---|
| Variable (unit) | Multivariable adjusted | Also adjusted for bone mass |
| Estradiol < 5 pg/ml | 2.37 (1.27–4.45) | 1.92 (1.01–3.64) |
| SHBG (per 1 μg/dl increase) | 1.34 (0.92–1.95) | 1.25 (0.85–1.84) |
| 1,25(OH)$_2$vitamin D ≦ 23 pg/ml§ | 2.20 (1.00–4.80) | 2.16 (0.93–5.00) |
| Age (per 5 year increase) | 2.22 (1.50–3.28) | 2.09 (1.41–3.10) |
| Weight (per 10 kg increase) | 0.56 (0.39–0.79) | 0.67 (0.46–0.98) |
| Calcaneal bone mass (per SD decrease)† | | 1.61 (1.03–2.56) |

*All results are adjusted for other variables in the table. SD (standard deviation) of calcaneal bone mass is 0.098 g/cm$^2$.
§To convert values for 1,25-dihydroxyvitamin D to picomoles per liter, multiply by 2.4.

This association remained significant after adjusting for estradiol and SHBG levels (hazard ratio=2.2; 1.0 to 4.8). Further adjustment for serum creatinine made no difference (hazard ratio=2.3; 1.0 to 5.2).

After excluding women taking vitamin D supplements, levels of 25(OH)vitamin D (mean±SD) were significantly higher in samples drawn from January through June (28.4±10.2 ng/ml [83.6±25.5 nm/L]) than from July through December (25.5±10.4 ng/ml [63.6±25.9 nm/L], P<0.01). There were no significant differences when vitamin D levels in April–September were compared with those drawn October–March. There were no statistically significant associations between low serum levels of 25(OH)vitamin D and risk of hip or vertebral fractures (see, Table 2), even after adjusting for month, season, or clinic, or whether women taking vitamin D supplements were included or not.

Adding bone mass to multivariable models of hormones and risk of fracture only slightly weakened the strength of association between estradiol, SHBG and risk of hip or vertebral fracture. See, Tables 3 and 4. Adjusting for bone mass had no substantial effect on the strength of association between 1,25(OH)$_2$vitamin D and hip fracture or between estrone and vertebral fracture.

The combined data indicate that the risks of hip and vertebral fractures in women over age 65 increase substantially when serum concentrations of estradiol are below 5 pg/ml, the detection limit of the assay. About one-third of incident hip and vertebral fractures can be attributed to these extremely low levels of estradiol. Women with slightly higher levels of estradiol, in the range of 5 to 10 pg/ml, had a much lower risk of these fractures.

Women with undetectable concentrations of estradiol also had lower bone mass. However, adjusting for calcaneal bone mass only modestly attenuated the increased risk of fracture. This suggests that the association between very low levels of estradiol and risk of fractures is at least partly independent of bone mass.

SHBG levels also exerted a strong and independent effect on the risks of hip and vertebral fractures. Women with concentrations of SHBG≧1.0 μg/dl and undetectable estradiol levels had more than a seven-fold greater risk of hip and vertebral fracture than women with lower SHBG and higher estradiol levels. SHBG avidly binds circulating estradiol, so that increased SHBG levels would be associated with decreased bioavailability of estradiol. Thus, concentrations of bioavailable estradiol may be even more strongly associated with fractures than the levels of total estradiol that we measured in this investigation.

EXAMPLE 2

This example demonstrates a comparison of the effects of administering differing amounts of estrogen using a 7-day estrogen transdermal therapeutic system, on the prevention of bone loss in postmenopausal women.

1. Methods

Healthy, hysterectomized women, 45–65 years old, 1–5 years after menopause with a baseline bone mineral density (BMD) measured by dual energy x-ray absorptiometry (DEXA) at L2–L4 within 2.5 S.D. of the mean for normal women less than 45 years old were eligible. Subjects were randomized to 1 of 4 doses of estradiol TTS (patches of 6.5, 12.5, 15, and 25 cm$^2$ delivering 0.025, 0.05, 0.06, and 0.1 mg/day estradiol, respectively) or placebo. One patch per week was worn on the abdomen for the duration of the 2-year trial. BMD at L2–L4, the femoral neck and forearm, serum osteocalcin (OST) and urinary deoxypyridinoline crosslinks/creatinine ration (DPD) were measured every 6 months. The results after 18 months treatment are presented.

2. Results 176 women, mean age 51.2 years were enrolled. A total of 103 subjects completed 18 months of treatment. Loss of BMD was prevented by all doses at all time points. At 18 months, placebo-treated patients had a mean percent change in lumbar BMD of −0.7±4.1 vs. 3.6±4.7, 3.2±3.1, 3.0±3.6 and 4.8±5.5 for the 0.025, 0.05, 0.06, and 0.1 mg/day groups, respectively (all differences p<0.05 vs. placebo). At 12 months, OST levels had fallen from baseline in all active treatment groups (percent changes of −30.4±42.9, −17.9±50.7, −13.0±37.6 and −26.9±29.8, respectively; all differences p<0.05 vs placebo +27.6±60.4). DPD also fell from baseline at 12 months in all active treatment groups (changes of −5.8±3.4, −6.0±8.5, −5.1±7.4 and −1.8±10.8 nmol/mmol, respectively). Three of the four active treatments were significantly different from placebo. However, DPD also fell in placebo-treated subjects.

3. Conclusions

Transdermal estradiol from both currently available strengths of CLIMARA® TTS (0.05 and 0.1 mg/day) as well as from a 6.5 cm$^2$ low-dose CLIMARA® TTS delivering 0.025 mg/day prevents postmenopausal bone loss. It is expected that a CLIMARA® TTS patch that delivers 10–15 μg per day would have effects on skeletal bone loss.

EXAMPLE 3

The following example and data demonstrate the correlation between serum estradiol level and loss of bone mineral density. The example also demonstrates the efficacy of using an ultra-low dose of exogenous estrogen to reduce loss of bone mineral density.

1. Experimental Population

Subjects were participants in the Study of Osteoporotic Fractures (SOF), the details of which have been described in Example 1. This study is based upon a randomly sampled subcohort of 261 SOF participants who had blood drawn and had technically adequate calcaneal BMD measured at both the baseline examination and at follow-up in 1993–94. Among these, 241 women had technically adequate hip bone mineral density measurements both at the year 2 examination in 1990 and at follow-up in 1993–94. Final results are based upon subcohorts of 231 and 218 women with complete calcaneal and hip BMD scan pairs, respectively, who did not report current use of estrogen replacement therapy during the base line interview. Sample sizes for individual assays vary due to missing values. Also, sample sizes are smaller for estradiol than for other assays because we added estradiol to the set of assays some time after the study was underway.

2. Measurements

At the baseline visit in 1986–1988, a detailed questionnaire was administered in which subjects were asked about current or previous use of estrogen, calcium and multivitamins containing vitamin D. Subjects were examined to obtain height and weight measurements.

Calcaneal bone mass was measured using single photon absorptiometry at baseline and at a follow-up visit in 1993–1994, after an average of 5.9 years. Bone density of the hip and its subregions were measured using dual x-ray absorptiometry at a second visit in 1988–1990, among 82% of the original cohort who survived. Repeat hip bone density was measured at follow-up in 1993–1994, after an average of 3.5 years. The mean coefficients of variation (CV) of 1.2% between centers for both the calcaneus and femoral neck were estimated using multiple measurements on staff members who visited each site. Spine bone density measurements were not performed on a sufficient number of subjects to warrant inclusion in this study.

3. Serum Samples

At the baseline examination, blood was drawn between 8:00 AM and 2:00 PM and sera stored at −20° C. Within two weeks, samples were shipped to Biomedical Research Institute (Rockville, Md.) and stored in liquid nitrogen at −190° C. In 1994, sera for selected participants was thawed and assayed for levels of circulating hormones and other biochemical measurements. Laboratories performing the assays were blinded to the participant's fracture status.

The stability of selected hormone measurements over time were determined in 51 women by testing levels of baseline and retesting again after 3.5 years of storage at −190° C. Correlations between the measurement pairs were as follows: estrone (r=0.98), total testosterone (r=0.99), mid-region parathyroid hormone (r=0.99) and 25(OH)D (r=0.88). All correlations were significant at p<0.001. At the time the baseline measurements were made, an immunoradiometric assay for PTH was not available. The correlation between PTH (IRMA) and mid-region in the samples measured after 3.5 years of storage was 0.78. Mean hormone levels did not differ substantially between the two samples.

4. Biochemical Assays

Serum concentrations of estradiol, estrone and total testosterone were measured by radioimmunoassay. The binding capacity of sex hormone binding globulin was measured using a displacement technique. Free testosterone levels were calculated as the product of total testosterone and the percent of non-SHBG bound steroid as determined from an ammonium sulphate precipitation procedure. Intact parathyroid hormone, 25(OH)D and 1,25(OH)$_2$D were measured by radioimmunoassay. Precision for all assays is reported in Table 5, along with descriptive data on the means and standard deviations as well as the quartile ranges for each hormone.

5. Statistical Analyses

All biochemical variables except estradiol were analyzed by quartiles and as continuous variables. Since 36% of estradiol levels were less than the minimum level of detection (5 pg/mL), estradiol values were divided into four groups by setting the undetectable levels as the lowest category and dividing the remaining detectable levels into tertiles. Estradiol categories are reported as quartiles in the tables for simplicity. For continuous models, undetectable estradiol levels were assigned zero values.

Linear regression analysis was used to analyze the association between hormone levels and the annual percent change in BMD, adjusting for age and weight. Results for annual absolute change in BMD and including clinic site as a covariate were similar and are not presented. Associations between hormone levels and bone loss were weaker for the femoral neck, and similar for the trochanteric regions compared with the total hip, and therefore we present results only for total hip bone loss. Age and weight-adjusted average percent change in BMD and 95% confidence intervals were calculated by quartiles of each hormone using the least squared means procedure, and a test for trend across quartiles (adjusting for age and weight) was used to assess statistical significance. The association between continuous hormone levels and annual percent change in BMD are reported as standardized beta coefficients, representing the difference in annual percent change in BMD per standard deviation increase in the level of each hormone.

Multivariable models were constructed to determine which biochemical variables were independent predictors of bone loss after controlling for levels of other hormones. Since estradiol and estrone levels are modestly correlated in this cohort (r=0.64), these variables were only analyzed in separate models.

6. Results

Characteristics of the random subsample used in this study are set forth in Table 2, and did not differ substantially from those of the cohort from which the sample was drawn. The mean age of women in this subsample was 71.3 years. Average annual bone loss was approximately 1.5 percent from the calcaneus and 0.5 percent from both the total hip and femoral neck.

TABLE 5

Descriptive Data on Biochemical Assays

| Factor | Intra-assay correlation | Inter-assay variability (%) | N* | Mean (SD) | Lowest quartile[†] | Q2[†] | Q3[†] | Highest quartile[†] |
|---|---|---|---|---|---|---|---|---|
| Sex steroids & SHBG | | | | | | | | |
| Estrone (ng/dL) | 0.97 | 8–12.5 | 230 | 2.3 (1.2) | <1.6 | 1.6–<2.3 | 2.3–<3.0 | ≧3.0 |
| Estradiol (pg/mL) | 0.96 | 6.2–7.0 | 168 | 6 (5) | <5 | 5–<7 | 7–<10 | ≧10 |
| Free testosterone (pg/ml) | 0.79 | 10.7–15.5 | 230 | 2.2 (1.9) | <0.9 | 0.9–<1.5 | 1.5–<2.7 | ≧2.7 |
| Total Testosterone (ng/dl) | 0.97 | 6.1–13.4 | 230 | 20.2 (15.7) | 9.7 | 9.7–<17.0 | 17.0–<26.0 | ≧26.0 |
| SHBG (µg/dl) | 0.95 | 4.1–14.4 | 230 | 1.5 (0.8) | <1.1 | 1.1–<1.5 | 1.5–<2.4 | ≧2.4 |
| Calciotropic Hormones and Calcium | | | | | | | | |
| PTH (pg/ml) | — | 8.5 | 231 | 34.3 (23.7) | <23 | 23–<31 | 31–<41 | ≧41 |
| 25(OH)D (pg/ml) | — | 15.0 | 231 | 26.2 (9.8) | <21 | 21–<25 | 25–<32 | ≧32 |
| 1,25(OH)$_2$D (pg/ml) | — | 12.4 | 229 | 32.9 (9.7) | <26 | 26–<32 | 32–<40 | ≧40 |
| Calcium (mg/dl) | — | — | 231 | 9.7 (0.5) | <9.5 | 9.5–<9.8 | 9.8–<10.0 | ≧10.0 |

*N, mean (SD) and quartile cutpoints were calculated for the calcaneal bone loss cohort. N's for the total hip bone loss cohort are report in Table 4.
[†]Range of values for indicated quartile.

TABLE 6

Characteristics of Participants in Calcaneal Bone Loss Cohort

| Characteristic | Calcaneal bone loss cohort, biochemical sample |
|---|---|
| Number | 231 |
| Age, years, mean (SD) | 71.3 (4.8) |
| Weight, kgs., means (SD) | 68.1 (11.7) |
| Current calcium supplements, n (%) | 102 (44.2) |
| Current vitamin D supplements, n (%) | 100 (44.1) |
| Dietary calcium, mg/day, mean (SD) | 687 (390) |
| Physical activity, kcal/week, mean (SD) | 1698 (1791) |
| Calcaneal BMD, g/cm$^2$, mean (SD) | 0.409 (0.088) |
| Total hip BMD, g/cm$^2$, mean (SD) | 0.765 (0.124) |
| Femoral neck BMD, g/cm$^2$, mean (SD) | 0.658 (0.108) |
| Spine BMD, g/cm$^2$, mean (SD) | 0.850 (0.154) |
| Calcaneal bone loss, %/year, mean (SD) | 1.48 (1.80) |
| Total hip bone loss, %/year, mean (SD) | 0.49 (1.49) |
| Femoral neck bone loss, %/year, mean (SD) | 0.50 (1.70) |

Associations of Hormones with Calcaneal BMD change are reported in Table 7. In age and weight adjusted linear regression models, only SHBG was a significant predictor of calcaneal bone loss.

TABLE 7

Associations of Hormones with Calcaneal BMD Change
Adjusted* Annual Average Percent Change in BMD (95% CI)

| Factor | Difference per SD increase ¥ | Lowest quartile | Q2 | Q3 | Highest quartile |
|---|---|---|---|---|---|
| Sex steroids & SHBG | | | | | |
| Estrone (ng/dl) | 0.2 (0.0, 0.5)† | −1.7(−2.1, −1.2) | −1.5(−1.9, −1.0) | −1.6(−2.0, −1.1) | −1.0(−1.5, −0.6) |
| Estradiol (ng/dl) | 0.2 (−0.1, 0.5) | −1.6(−2.0, −1.1) | −1.3(−1.9, −0.6) | −1.3(−1.9, −0.8) | −1.0(−1.7, −0.3) |
| Free testosterone (pg/ml) | 0.1 (−0.1, 0.4) | −1.9(−2.4, −1.3) | −1.4(−1.9, −1.0) | −1.6(−2.1, −1.2) | −1.2(−1.6, −0.7) |
| Total Testosterone (ng/dl) | 0.0 (−0.2, 0.2) | −1.5(−1.9, −1.0) | −1.8(−2.3, −1.4) | −1.2(−1.7, −0.8) | −1.3(−1.8, −0.9) |
| SHBG (μg/dl) | −0.6 (−0.8, −0.3)‡ | −1.2(−1.6, −0.7) | −1.2(−1.6, −0.7) | −1.7(−2.2, −1.3) | −2.2(−2.9, −1.6)‡ |
| Calciotropic Hormones and Calcium | | | | | |
| PTH (pg/ml) | 0.0 (−0.2, 0.2) | −1.3(−1.7, −0.8) | −1.5(−1.9, −1.0) | −1.6(−2.0, −1.1) | −1.6(−2.1, −1.2) |
| 25(OH)D (pg/ml) | −0.1 (−0.3, 0.1) | −1.2(−1.7, −0.8) | −1.8(−2.3, −1.4) | −1.3(−1.8, −0.8) | −1.5(−2.0, −1.0) |
| 1,25(OH)$_2$D (pg/ml) | 0.0 (−0.2, 0.2) | −1.3(−1.8, −0.8) | −1.6(−2.0, −1.2) | −1.7(−2.1, −1.2) | −1.3(−1.8, −0.8) |
| Calcium (mg/dl) | 0.1 (−0.2, 0.3) | −1.4(−1.8, −0.9) | −1.6(−2.1, −1.2) | −1.4(−2.0, −0.9) | −1.5(−1.9, −1.1) |

*Adjusted for age and weight, excluding ERT users.
¥Difference in annual percent change in BMD per SD increase in level of hormone/factor.
†p < 0.10
§p < 0.05
‡p < 0.01
Significance tests for differences per SD are based upon the test $H_o$: $\beta = 0$ on the linear parameter estimate for each hormone.
Significance tests across quartiles are based upon tests for trend.

Women with SHBG levels in the highest quartile (≧2.4 μg/dL) experienced twice as much calcaneal bone loss annually (mean change=−2.2 percent; 95% CI=−2.9%, −1.6%) compared with women with levels in the lowest quartile (<1.1 μg/dL; mean change=−1.2%; −1.6%, −0.7). This association remained strongly significant even after adjustment for levels of serum estradiol, estrone and testosterone (p<0.002). Trends towards increased calcaneal bone loss with decreasing hormone levels are apparent for all sex steroids (see, Table 7), but none were statistically significant. There was a borderline (p<0.10) inverse statistical association between serum estrone concentrations modeled as a continuous variable and calcaneal bone loss.

The data regarding the associations of hormones with total hip BMD change (see, Table 8) demonstrate that lower levels of both estrone and estradiol were significantly associated with greater hip bone loss.

TABLE 8

Associations of Hormones with Total Hip BMD Change.
Adjusted* Annual Average Percent Change in BMD (95% CI).

| Factor | N | Difference per SD increase¥ | Lowest quartile | Q2 | Q3 | Highest quartile |
|---|---|---|---|---|---|---|
| Sex steroids & SHBG | | | | | | |
| Estrone (pg/ml) | 217 | 0.2(0.0, 0.4)† | −0.8(−1.2, −0.4) | −0.7(−1.1, −0.3) | −0.3(−0.7, 0.2) | −0.1 (−0.5, 0.3)‡ |
| Estradiol (pg/ml) | 160 | 0.2(0.0, 0.5) | −0.8(−1.2, −0.3) | −0.8(−1.2, −0.2) | −0.3(−0.7, 0.2) | 0.1 (−0.5, 0.7)§ |
| Free testosterone (pg/ml) | 217 | 0.3(0.0, 0.5)¥ | −0.6(−1.0, −0.1) | −0.5(−0.9, −0.1) | −0.7(−1.1, −0.3) | −0.3 (−0.6, 0.1) |
| Total Testosterone (ng/ml) | 217 | 0.1(−0.1, 0.3) | −0.6(−0.9, −0.2) | −0.6(−1.0, −0.3) | −0.6(−1.0, −0.2) | −0.1 (−0.5, 0.3) |
| SHBG (μg/dl) | 217 | 0.1(−0.4, 0.1) | −0.4(−0.7, −0.1) | −0.4(−0.7, 0.0) | −0.7(−1.7, −0.3) | −0.7 (−1.2, −0.1) |
| Calciotropic Hormones and Calcium | | | | | | |
| PTH (pg/ml) | 218 | 0.2(0.0, 0.4)¥ | −0.4(−0.8, 0.0) | −0.6(−1.0, −0.2) | −0.6(−1.0, −0.2) | −0.3 (−0.7, 0.1) |
| 25(OH)D (pg/ml) | 218 | 0.2(0.0, 0.4)¥ | −0.7(−1.1, −0.4) | −0.6(−0.9, −0.2) | −0.5(−0.9, −0.1) | −0.1 (−0.5, 0.3)§ |
| 1,25(OH)₂D (pg/ml) | 216 | 0.0(−0.2, 0.2) | −0.5(−1.0, −0.1) | −0.6(−0.9, −0.2) | −0.5(−0.9, −0.1) | −0.4 (−0.7, 0.0) |
| Calcium (mg/dl) | 218 | 0.2(0.0, 0.3) | −0.4(−0.7, 0.0) | −0.7(−1.1, −0.4) | −0.5(−1.0, −0.1) | −0.3 (−0.7, 0.0) |

*Adjusted for age and weight, excluding ERT users.
¥Difference in annual percentage change in BMD per SD increase in level of hormone/factor.
†p < 0.10
¥p < 0.05
‡p < 0.01
Significance tests for difference per SD are based upon the test $H_o$: $\beta$ = O on the linear parameter estimate for each hormone
Significance tests across quartile are based upon tests for trend.

For example, after adjusting for age and weight, women with estradiol levels 10 pg/mL or higher experienced a slight increase in bone mass during follow-up (mean annual change=0.1 percent; −0.5, −0.7), while women with estradiol levels below 5 pg/mL experienced above average rates of hip bone loss (mean annual change=−0.8 percent; −1.2, −0.3).

Examination of the mean annual percent change in hip bone density by quartiles of testosterone levels suggested a threshold: women with total testosterone levels 26 ng/dL or higher (highest quartile) experienced an average annual percent change of only −0.1% (−0.5%, 0.3%) compared with −0.6% (−0.8%, −0.4%) among women with below 26 ng/dL (quartiles 1 through 3 combined). This difference was statistically significant (p<0.05). An increase in hip bone loss across quartiles of SHBG was observed, although this trend was not statistically significant in age and weight adjusted regression models (p=0.27).

In a multivariable model including SHBG, estradiol and testosterone levels in addition to age and weight, lower total testosterone and higher SHBG concentrations were independently associated with change in hip BMD. The data are reported in Table 9.

TABLE 9

Multivariable Model: sex hormones, SHBG and total hip bone loss
Difference in percent change in hip BMD*

| Factor | Adjusting for age and weight only¥ | Multivariable model† |
|---|---|---|
| SHBG (per SD increase) | −0.3 (−0.6, 0.0)‡ | −0.3 (−0.6, 0.0)‡ |
| Estradiol (per SD increase) | 0.2 (0.0, 0.5) | 0.1 (−0.1, 0.4) |
| Total testosterone (>25 ng/dL vs. others) | 0.6 (0.0, 1.2)‡ | 0.6 (0.0, 1.3)‡ |

*All analyses include only women who had estradiol measurements for comparability.
¥The first column presents results of separate regression models for each hormone, adjusted for age and weight.
†The second column presents results of a single regression model containing SHBG, estradiol, total testosterone, age and weight.
‡p < 0.05.

Because there were a substantial number of women who did not have estradiol measurements, it was unclear whether the significant association between SHBG and hip bone loss in the multivariable model resulted from adjustment for other hormone levels or whether a stronger association between SHBG and bone loss existed in this subcohort of women. Therefore, the age and weight adjusted association between SHBG and hip bone loss was reexamined among women who had estradiol measurements and was found to be statistically significant. See, Table 9.

When expressed as a continuous variable, estradiol was not significantly associated with change in hip BMD either before or after adjustment for testosterone and SHBG. However, the test for trend across quartiles of estradiol remained significant after controlling for levels of SHBG and testosterone, whereas the trend across estrone quartiles was of borderline significance (p<0.06).

Only 25(OH)D levels were significantly different during wintertime (January–June) compared with the remainder of the year (July–December), with mean values of 24.0 during the winter and 26.9 otherwise (p=0.01). There were no significant differences in calciotropic hormone levels comparing measurements taken May through October compared with November through April.

None of the calciotropic hormones or calcium levels were significantly associated with change in calcaneal BMD after controlling for age and weight. See, Table 7. This remained true even after adjustment for season (July–December versus January–June) and clinic, and after either adjustment for, or exclusion of, current users of calcium or multivitamins containing vitamin D.

Lower levels of 25(OH)D were significantly associated with increased hip bone loss. See, Table 9. Women with 25(OH)D levels in the highest quartile ($\geq$32 pg/mL) experienced an annual average change in BMD of −0.1 percent (−0.5, 0.3) compared with −0.7 (−1.1, −0.4) among women with 25(OH)D levels in the lowest quartile (<21 pg/mL). This trend remained significant after adjustment for clinic, season and use of calcium and multivitamnins containing vitamin D.

There was no consistent association between parathyroid hormone (PTH) levels and bone loss from either site. See, Tables 7 and 8. Examination of the trend across quartiles of PTH reveals an unusual pattern with greater hip bone loss for PTH levels in the central range (second and third quartiles) and less bone loss among women with more extreme values (lowest and highest quartiles).

7. Conclusion

The data demonstrate that lower levels of serum estrogens are significantly associated with increased hip bone loss in elderly women, even after controlling for age, weight and levels of SHBG and testosterone. In fact, women with estradiol levels 10 pg/mL or higher experienced on average a small increase in bone mass during follow-up (mean annual change=0.1%; 95% CI=−0.5, 0.7), while women with undetectable estradiol levels (<5 pg/mL) lost bone from the hip at the rate of almost one percent per year (−0.8%; −1.2, −0.3). Since bone loss may be an important risk factor for hip fracture in elderly women, these findings suggest that even moderate increases in levels of circulating hormones may be effective in reducing rates of bone loss and fractures.

SHBG concentrations were strongly associated with both calcaneal and hip bone loss, independent of age, weight and sex hormone levels. SHBG binds serum estradiol and testosterone with great affinity, and this association may reflect an increased risk of bone loss with decreasing levels of bioavailable sex hormones. However, the strength of this association even after adjusting for levels of serum estradiol and testosterone suggest that there may be other influences of SHBG on bone.

Lower 25(OH)D levels are related to more rapid bone loss from the hip, but not from the calcaneus. Previous results of cross-sectional studies have been mixed: two studies have found postmenopausal women with lower 25(OH)D levels to have lower bone mineral density (see, Villareal, *J. Clin. Endocrin. Metab.* 72(3):628–634 (1991); Martinez et al., *Calcified Tissue International* 55(4):253–256 (1994)), but at least one other cross-sectional study found no significant association between 25(OH)D and bone mineral density at the distal radius, the mid-radius or the lumbar spine (see, Tsai et al., *Calcified Tissue International* 40(5):241–243 (1987)). However, the Tsai et al. study had a broad age range (33–94) and did not report associations separately for elderly women.

PTH levels were not associated with bone loss from the calcaneus or the hip in our study. This was true even after adjustment for season, and exclusion of women taking calcium or vitamin D supplements.

This study is a prospective study, measuring rates of change in bone mass rather than cross-sectional bone mass measurements. Serum samples were obtained prior to measurement of change in bone mass. The sample size was considerable larger than in most other related studies, and the subjects were sampled from a cohort of elderly women living in four separate communities in the United States.

In conclusion, the results demonstrate that SHBG and endogenous estrogens are important determinants of bone loss in elderly women. Lower 25(OH)D levels are associated with more rapid bone loss from the hip, but not from the calcaneus. PTH and other calciotropic hormones do not significantly influence bone loss in elderly women.

EXAMPLE 4

The following example and data demonstrate the correlation between serum estradiol levels and bone density.

1. Experimental Population

Subjects in this analysis were participants in the Study of Osteoporotic Fractures (SOF), which is described in Example 1.

All 9704 SOF participants were interviewed and examined at 1 of the clinical centers during the baseline visit in 1986–1988. At that visit, detailed data about physician-diagnosed medical conditions and past medications were collected. WE obtained standardized assessments of height, weight, and strength. We measured BMD of the calcaneus and proximal third of the radius by using single photon absorptiometry. Lateral radiographs of the thoracic and lumbar spine were obtained. Serum samples were collected from each participant.

Participants completed questionnaires annually and had 3 biennial follow-up visits to the clinic. At the first follow-up visit (conducted during 1988–1990), we measured BMD of the proximal end of the femur using dual-energy x-ray absorptiometry (DXA). Details of these measurement methods and quality control procedures for densitometry are described in Steiger et al., *J. Bone Miner. Res.* 7:625–632 (1992).

2. Serum Samples and Biochemical Tests

All participants were instructed to adhere to a fat-free diet overnight and to minimize lipemia on the morning of the examination which would interfere with assays. Blood was drawn between 8 am and 2 pm and serum was frozen at −20° C. Within 2 weeks, all samples were shipped to the Biomedical Research Institute (Rockville, Md.), where they were stored in liquid nitrogen (approximately −190° C.). The long-term stability of these samples was determined by comparing estradiol results obtained after 2 weeks storage at −20° C. with those obtained after 3.5 years storage at −190° C.; for 51 samples, the correlation coefficient was 0.94, and the means (±SD) were 11.8 (9.0) after 2 weeks and 10.9 (9.0) after 3.5 years.

In the initial cohort studied, biochemical tests using baseline serum were available from 400 randomly selected participants. For this analysis, we excluded women for whom we did not have measures of serum estradiol (n=134) and those who reported current use of systemic estrogen therapy (n=39); 247 women remained available for the current analysis.

The following biochemical analyses were performed for each subject: calcitropic factors included calcium, 25-hydroxyvitamin D, 1.25-dihydroxy vitamin D, and parathyroid hormone; growth factors included insulin-like growth factor-1 and insulin-like growth-factor-binding protein 3; bone formation markers included bone-specific alkaline phosphatase and osteocalcin; sex and adrenal hormones included estradiol, estrone, testosterone (total and free), SHBG, dehydroepiandrosterone sulfate (DHEAS); other endocrine tests included thyroid-stimulating (TSH). Methods for these biochemical analyses are described in Reginster et al., *Calcif. Tissue Intl.* 51:340–343 (1992). The immunoassays for estradiol were performed by Endocrine Sciences Laboratory (Tarzana, Calif.), which used highly sensitive assay with a 5-pg/mL lower limit of detection.

To validate our findings in an independent cohort, we measured baseline serum estradiol from a second random sample of 222 SOF participants who satisfied the same inclusion and exclusion criteria as the initial analysis sample. Serum estradiol measurements in the second cohort were performed at Corning Nichols Institute (San Juan Capistrano, Calif.), which used highly sensitive assay with a 2-pg/mL lower limit of sensitivity. Results from 22 split-serum specimens measured at the 2 reference laboratories showed similar results (correlation coefficient=0.9, slope 1.3).

3. Ascertainment of Vertebral Deformity

Radiographic morphometry was used to diagnose prevalent vertebral deformity at baseline; criteria for prevalent deformity was >3 SD reduction in either antero-, mid-, or postervertebral height of at least 1 vertebra. See, Black et al., *J. Bone Miner. Res.* 10:890–902 (1995).

4. Statistical Analyses

Analyses were done at the SOF Coordinating Center at the University of California, San Francisco.

In the first sample (n=247), the women were stratified into 4 groups based on their serum estradiol level: in 1 stratum all women with undetected estradiol (<5 pg/mL, n=81, 32.8%) were included; the remaining women were stratified into 3 roughly equal groups on the basis of estradiol levels of 5–6 pg/mL, 7–9 pg/mL, and 10–25 pg/mL; number of subjects in these strata was 55 (22.3%), 63 (25.5%), and 48 (19.4%). In the second (validation) sample (n=222), the same serum estradiol cutpoints were used; the proportion of subjects in these strata was 25.2%, 27.5%, 24.8%, and 22.5%.

The outcomes were examined, adjusting for subjects' weight and age. Because weight and BMI are highly correlated and because weight shows the stronger relation with BMD. See, Bauer et al., *Ann. Intern. Med.* 118:657–665 (1993). We selected weight for inclusion in subsequent models. We then evaluated the possible contribution of covariates by first examining variables we considered to be potential predictors of bone density or osteoporotic fracture. If any potential confounder showed a consistent trend (analysis of variance with test for linear trend) across the strata of estradiol, we further valuated its effects in multivariate models for which outcomes were bone density at the four skeletal sites of interest. These models included age, clinic site, and serum estradiol as well as the candidate predictor variable. If the candidate variable was retained in most of these models, it was considered a confounder. We also added to the model grip strength and current smoking because these variables proved in our prior studies to be predictors of BMD (see Bauer et al., *Ann. Intern. Med.* 118:657–665 (1993)) and fracture (see Cummnings et al., *N. Engl. J. Med.* 332:767–773 (1995)).

Using analysis of variance, the adjusted mean BMD was calculated for each stratum of estradiol. Dunnett's test was used to determine the statistical significance of difference between the adjusted BMD of the lowest stratum (undetectable estradiol) versus each of the 3 higher strata. The logistic regression model was used to calculate multiple-adjusted odds ratio (OF) and the 95% confidence intervals for risk of prevalent vertebral deformity for each of the 3 higher strata of estradiol versus the lowest stratum. Analyses were performed using SAS (SAS Institute, Cary, N.C.).

5. Subject Characteristics by Estradiol Level

Clinical measurements of the women in this study are set forth in Table 10.

TABLE 10

Clinical and laboratory values measured in 247 elderly women grouped by serum estradiol level

| | SERUM ESTRADIOL LEVEL | | | | |
|---|---|---|---|---|---|
| For Variable | Undetectable (n = 81) | 5–6 pg/mL (n = 55) | 7–9 pg/ml (n = 63) | 10–25 pg/mL (n = 48) | P value Linear Trend |
| Mean (SD) | | | | | |
| Age, yr | 71.8 (4.8) | 72.9 (4.8) | 71.1 (4.8) | 71.8 (5.7) | .57 |
| Height, cm | 158.9 (6.1) | 159.9 (6.1) | 158.1 (5.4) | 159.1 (6.3) | .84 |
| Weight, kg | 65.2 (10.3) | 65.0 (11.3) | 69.9 (11.3) | 77.3 (15.4) | <.001 |
| Waist: hip girth ratio | 0.81 (0.08) | 0.82 (0.06) | 0.81 (0.06) | 0.83 (0.08) | .08 |
| Grip strength, kg | 21.6 (4.5) | 20.5 (4.6) | 22.8 (4.7) | 21.5 (5.3) | .48 |
| Estrone level, pg/mL | 16.8 (8.7) | 18.3 (8.6) | 25.3 (7.4) | 38.4 (13.6) | <.001 |
| Testosterone level, ng/dL | 13.9 (11.1) | 16.7 (9.6) | 20.5 (15.5) | 27.0 (15.3) | <.001 |
| Osteocalcin level, ng/mL | 25.8 (10.5) | 25.2 (9.1) | 24.9 (9.8) | 23.0 (12.7) | .17 |
| SHBG level, $\mu$/dL | 1.7 (1.0) | 1.6 (0.9) | 1.4 (0.7) | 1.4 (0.6) | .01 |
| Percentage | | | | | |
| Health not good | 21 | 11 | 11 | 15 | .22 |
| >1 fall in past year | 33 | 20 | 26 | 29 | .59 |
| Smoking, current | 7 | 9 | 5 | 9 | .11 |
| Calcium intake <400 mg | 11 | 20 | 14 | 4 | .32 |
| Diabetes mellitus | 9 | 9 | 10 | 13 | .52 |
| Thiazide use, current | 23% | 15% | 27% | 36% | .07 |

TABLE 10-continued

Clinical and laboratory values measured in 247 elderly women grouped by serum estradiol level

| | SERUM ESTRADIOL LEVEL | | | | |
|---|---|---|---|---|---|
| For Variable | Undetectable (n = 81) | 5–6 pg/mL (n = 55) | 7–9 pg/ml (n = 63) | 10–25 pg/mL (n = 48) | P value Linear Trend |
| Thyroidhormone use, current | 7 | 17 | 11 | 15 | .28 |
| >10-year estrogen use before study | 8 | 11 | 10 | 11 | .69 |

On average, the women in this study were aged about 72 years (Table 10). Mean estradiol did vary with age; those aged 65–74 years had mean (SD) estradiol 5.8 (5.1) pg/mL compared with 6.3 (4.9) pg/mL for those $\geq 80$ years. Height did not differ across estradiol strata. Body weight was statistically significantly higher among women in the highest estradiol stratum. Biochemical tests which did not show large or consistent differences across estradiol strata included calciotropic factors, growth factors, bone-specific alkaline phosphatase, and DHEAS (results not shown). Estrone and total testosterone were about twofold higher in women with the highest estradiol levels compared with those with undetectable estradiol. Several variables, including those relating to body weight, those striking and consistent difference across estradiol strata. Osteocalcin tended to be lower at higher levels of estradiol; the highest stratum was 10.9% lower than the lowest (undetectable) stratum of estradiol. Because they also showed difference across estradiol strata and fairly consistent relations to the 4 BMD outcomes, weight and SHBG were included in the model along with age, grip strength, and current smoking.

Age- and weight-adjusted baseline BMD of all four skeletal sites showed a similar trend to be higher with higher levels of estradiol. Compared with women with <5 pg/mL serum estradiol, those with levels 10–25 pg/mL had statistically significantly greater mean BMD at all skeletal sites; the difference was 4.6%, 6.1%, 5.8%, and 7.1% for the total hip, calcaneus, proximal radius, and spine (p<0.05 for each comparison). After multiple adjustment, the difference remained statistically significant: 5.7%, 6.3%, 6.5%, and 6.9% for the total hip, calcaneus, proximal radius, and spine.

The women in the validation study showed similar characteristics to the women in our initial study, including serum estradiol levels. Similar associations between serum estradiol level and BMD were found in the validation cohort. Age- and weight-adjusted BMD at all four skeletal sites showed a trend similar to the original cohort. Compared with women who had <5 pg/mL serum estradiol, those with levels 10–25 pg/mL had 4.9%, 9.6%, 7.3%, and 6.8% greater BMD at the total hip, calcaneus, proximal radius, and spine. After multiple adjustment, the difference remained statistically significant: 3.8%, 7.0%, 5.4%, 6.9% greater BMD at the total hip, calcaneus, proximal radius, and spine.

Of women in the lowest estradiol stratum (<5 pg/mL), 30% had $\geq 1$ prevalent vertebral deformities in contrast to lower prevalence in the other three strata which ranged from 7–19%. After age and weight adjustment, prevalent vertebral deformities were 60% less likely among women with estradiol levels between 5–25 pg/mL compared with those who had undetectable estradiol levels (OR=0.4, 95% confidence interval (CI) 0.2–0.8); this ratio was minimally affected by multiple adjustment (OR=0.4, CI 0.2–0.7). In the validation cohort, we did not find any trend toward an association between estradiol level and prevalence of vertebral deformity; prevalence was similar across all strata and ranged from 15% to 19%.

6. Conclusions

The data demonstrate that serum estradiol levels below 5 pg/mL are detrimental to skeletal health in older women. After age and weight adjustment, the data show that women with estradiol <5 pg/mL had substantially less BMD at all skeletal sites. Additionally, the data show that osteocalcin, an indicator of bone turnover, tends to be higher in women with lower serum estradiol levels. Thus, low levels of estradiol exert clinically important effects on the skeleton of an elderly woman. A likely explanation is that estradiol, when present in low concentrations, reduces skeletal remodeling, allows for both better quality and mass of bone, and thereby reduces fracture rates.

The difference in BMD that we observed was substantial and corresponded to about 0.4 standard deviations (SD) even after adjusting for multiple factors. This difference would be expected to reduce by 30% the risk of hip fracture (assuming 1.0 SD=0.11 g/cm$^2$ and 1.0 SD difference=RR 2.8). Using similar calculations, we estimate that the spine density benefit associated with serum estradiol 10–25 pg/mL, equivalent to about 0.4 SD, would be expected to reduce the risk of spine fracture by 23% (assuring 1.0 SD=0.17 g/cm$^2$ and 1.0 SD difference=RR 2.1).

Estrone has been widely examined as a predictor of skeletal health among postmenopausal women. BMD has been found to be cross-sectionally related to serum estrone levels in both white and black women. (see, Cauley et al., Am. J. Epid. 139:1035–1046 (1994)) However, this study was limited because estradiol levels were below the limit of detection in more than half of the women. Estrone was not predictive of incident hip fractures. In postmenopausal women, estrone is quantitatively the predominant estrogen and is produced mainly from conversion of adrenal androstenedione. Estradiol is produced through reduction of estrone and through aromatization of ovarian and adrenal testosterone, which is derived from conversion of androstenedione and DHEA. (See, Cauley et al., Am. J. Epid. 139:1035–1046 (1994)). The data show a relatively high correlation between serum levels of estrone and estradiol both in the initial sample (r=0.65) and in the validation sample (r=0.78). Estradiol, not estrone, is believed to be the effector hormone at the nuclear receptor. (See, Grodin et al., J. Clin. Endo. Metab. 36:207–214 (1973)). Estradiol is also 4 to 10 times more potent than estrone. That estradiol was the major sex steroid hormone which had a strong, consistent, and positive relation to skeletal outcome could therefore be expected.

Estradiol could produce beneficial skeletal effects through several possible mechanisms: it reduces activation of bone metabolic units; it antagonizes parathyroid hormone's stimulation of bone resorption; it may enhance survival of osteoblasts via local cytokines or other growth factors; it improves both efficiency of gastrointestinal calcium absorption and renal calcium conservation. Some or all of these actions may be responsive to very low levels of estradiol. Our data also support estradiol's effect on reduction of bone turnover. Indirectly, estradiol could influence bone through body weight, but our data adjusted for body weight and still found a strong association.

In the past, study of estradiol's effects has been hampered by insensitive assays. Only very sensitive and precise methods can distinguish between low (<30 pg/mL) and very low (<5 pg/mL) estradiol levels. Few commercial laboratories provide estradiol assays which have lower limits of detection below 20 pg/mL. Lack of such sensitive assays may have hindered others from finding these associations. The impact of low versus very low endogenous estradiol production is subtle and could take many years to manifest differences in BMD. Our cross-sectional data suggest that estradiol levels do not decrease with aging after age 65 yr.

Our results indicate a protective effect of low levels of estradiol against low bone mass and fracture; this effect is consistent because it can be observed for bone density at several skeletal sites, for bone loss at the hip and calcaneus, and for spine fracture risk. These findings were reproduced by using a different laboratory's highly sensitive estradiol assay. Estradiol's beneficial skeletal effects in the elderly occur at levels which have been previously believed to have no physiologic impact.

The foregoing description of the preferred embodiments and examples are illustrative of the present invention and are not to be construed as limiting thereof. The invention is defined by the following claims, with equivalents of the claims to be included therein.

That which is claimed is:

1. A method for treating a physical condition resulting from estrogen decline in a postmenopausal subject, said method comprising administering to said subject an amount of estrogen which is effective to produce a resulting serum level of said estrogen in said subject that is equivalent to a serum estadiol level not exceeding of between about 5 pg/ml and about 15 pg/ml, wherein:

the estrogen is administered orally, parenterally, or transdermally; said physical condition is selected from the group consisting of osteoporosis, headaches, nausea, depression, hot flashes, decrease in bone mineral density, and increased risk or incidence of bone fracture; and the resulting serum level of the estrogen is responsive to the administering of the estrogen.

2. The method of claim 1, wherein said physical condition is selected from the group consisting of postmenopausal estrogen decline, increased risk of osteoporotic bone fracture due to postmenopausal osteoporosis, and loss of bone mineral density.

3. The method of claim 1, wherein said amount of estrogen which is administered is effective to produce a serum level of said estrogen equivalent to a serum estradiol level in said subject of between about 5 pg/ml and about 10 pg/ml.

4. The method of claim 1, wherein said estrogen is estradiol.

5. The method of claim 4, comprising orally administering said amount of estrogen.

6. The method of claim 5, wherein said amount of estrogen administered is less than 0.5 mg/day.

7. The method of claim 5, wherein said amount of estrogen administered is between 0.1–0.25 mg/day.

8. The method of claim 4, comprising parenterally administering said amount of estrogen.

9. The method of claim 8, wherein said amount of estrogen administered is less than about 20 $\mu$g/day.

10. The method of claim 8, wherein said amount of estrogen administered is between 5–15 $\mu$g/day.

11. The method of claim 8, wherein said amount of estrogen administered is about 10 $\mu$g/day.

12. The method of claim 4, comprising transdermally administering said amount of estrogen.

13. The method of claim 12, wherein said amount of estrogen administered is not more than about 15 $\mu$g per day.

14. The method of claim 12, wherein said amount of estrogen administered is between about 5 $\mu$g and about 15 $\mu$g per day.

15. A kit for use by a consumer afflicted with or susceptible to physical conditions resulting from postmenopausal estrogen decline, said kit comprising:

a) a transdermal patch for transdermally administering an estrogen in an amount that is equivalent to less than about 15 $\mu$g of estradiol per day; and b) instructions describing a method of using the transdermal patch to reduce the risk of osteoporotic bone fracture in said consumer.

16. A method for treating a physical condition resulting from estrogen decline in a postmenopausal subject, said method comprising administering transdermally an estrogen in an amount that is equivalent to less than about 20 $\mu$g of estradiol per day to said subject, in the substantial absence of exogenous progestin, wherein serum level of said estrogen in said subject is equivalent to a serum estradiol level of between about 5 pg/ml and about 15 pg/ml, and wherein said physical condition is selected from the group consisting of osteoporosis, headaches, nausea, depression, hot flashes, decrease in bone mineral density, and increased risk or incidence of bone fracture.

17. The method of claim 16, wherein said physical conditions are selected from the group of postmenopausal estrogen decline, increased risk of osteoporotic bone fracture due to postmenopausal osteoporosis, and loss of bone mineral density.

18. The method of claim 16, wherein said administration is prior to hysterectomy of said subject.

19. The method of claim 16, wherein said estrogen is estradiol.

20. The method of claim 19, further comprising the step of testing the serum estradiol level of the subject and determining that the serum estradiol level of the subject to be treated is normal for postmenopausal women in the same age group as the subject.

21. The method of claim 19, wherein said amount of estrogen administered is between about 5 $\mu$g and about 15 $\mu$g per day.

22. The method of claim 19, wherein said amount of estrogen administered is about 10 $\mu$g per day.

23. The method of claim 19, wherein said amount of estrogen administered is about 15 $\mu$g per day.

* * * * *

UNITED STATES PATENT AND TRADEMARK OFFICE
CERTIFICATE OF CORRECTION

PATENT NO. : 6,692,763 B1
DATED : February 17, 2004
INVENTOR(S) : Cummings et al.

It is certified that error appears in the above-identified patent and that said Letters Patent is hereby corrected as shown below:

<u>Column 27,</u>
Line 39, please delete the phrase "not exceeding".

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,692,763 B1 | Page 1 of 1 |
| APPLICATION NO. | : 09/554789 | |
| DATED | : February 17, 2004 | |
| INVENTOR(S) | : Steven R. Cummings et al. | |

It is certified that error appears in the above-identified patent and that said Letters Patent is hereby corrected as shown below:

<u>Column 1,</u>
Line 5, before "BACKGROUND OF THE INVENTION," please insert the following:

-- STATEMENT REGARDING FEDERALLY SPONSORED RESEARCH OR DELEVELOPMENT
This invention was made with government support under Grant No. AG05407 awarded by the National Institutes of Health. The government has certain rights in the invention. --

Signed and Sealed this

Twenty-fourth Day of February, 2009

JOHN DOLL
*Acting Director of the United States Patent and Trademark Office*